US007566816B2

(12) United States Patent
Lightner et al.

(10) Patent No.: US 7,566,816 B2
(45) Date of Patent: Jul. 28, 2009

(54) GENERATION OF PLANTS WITH ALTERED OIL CONTENT

(75) Inventors: Jonathan Lightner, Des Moines, IA (US); Stephanie K. Clendennen, Kingsport, TN (US)

(73) Assignee: Agrigenetics, Inc., Indianapolis, IN (US)

( * ) Notice: Subject to any disclaimer, the term of this patent is extended or adjusted under 35 U.S.C. 154(b) by 295 days.

(21) Appl. No.: 10/539,213

(22) PCT Filed: Dec. 18, 2003

(86) PCT No.: PCT/US03/41146

§ 371 (c)(1), (2), (4) Date: Jan. 17, 2006

(87) PCT Pub. No.: WO2004/054351

PCT Pub. Date: Jul. 1, 2004

(65) Prior Publication Data

US 2006/0168685 A1    Jul. 27, 2006

Related U.S. Application Data

(60) Provisional application No. 60/434,763, filed on Dec. 18, 2002.

(51) Int. Cl.
*A01H 5/00* (2006.01)
*C12N 15/82* (2006.01)
(52) U.S. Cl. ........................ 800/298; 800/281
(58) Field of Classification Search .................. None
See application file for complete search history.

(56) References Cited

U.S. PATENT DOCUMENTS

| 5,639,790 A | 6/1997 | Voelker et al. |
| 5,704,160 A | 1/1998 | Bergquist et al. |
| 6,229,033 B1 | 5/2001 | Knowlton |
| 6,248,939 B1 | 6/2001 | Leto et al. |

FOREIGN PATENT DOCUMENTS

| WO | WO 99/32661 | 7/1999 |
| WO | WO 99/67367 | 12/1999 |

OTHER PUBLICATIONS

Doerks et al, TIG 14(6): 248-250, Jun. 1998.*
Brenner, S.E., TIG 15(4): 132-133, Apr. 1999.*
Bork et al, TIG 12(10): 425-427, Oct. 1996.*
Broun et al, Science 282: 1315-1317, Nov. 13, 1998.*
Alcaraz et al. Database Accession No. AL132972, 2000.
Anoop et al., "Modulation of citrate metabolism alters aluminum tolerance in yeast and transgenic canola overexpressing a mitochondrial citrate synthase," *Plant Physiol.*, 132:2205-2217, 2003.
Beisson et al., "*Arabidopsis* genes involved in acyl lipid metabolism. A 2003 census of the candidates, a study of the distribution of expressed sequence tags in organs, and a web-based database," *Plant Physiol.*, 132:681-697, 2003.
Bert et al., "Comparative genetic analysis of quantitative traits in sunflower (*Helianthus annuus* L.). 2. Characterisation of QTL involved in developmental and agronomic traits," *Theor. Appl. Genet.*, 107:181-189, 2003.
Colbert et al., "High-throughput screening for induced point mutations," *Plant Physiol.*, 126(2):480-484, 2001.
Dehesh et al., "Overexpression of 3-ketoacyl-acyl-carrier protein synthase IIIs in plants reduces the rate of lipid synthesis," *Plant Physiol.*, 125:1103-1114, 2001.
Eastmond and Graham, "Re-examining the role of glyoxylate cycle in oilseeds," *Trends Plant Sci.*, 6(2):72-77, 2001.
Eccleston and Ohlrogge, "Expressions of lauroyl-acyl carrier protein thioesterase in *Brassica napus* seeds induces pathways for both fatty acid oxidation and biosynthesis and implies a set point for triacylglycerol accumulation," *Plant Cell.* 10:613-621, 1998.
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in *Arabidopsis*," *Plant Cell*, 17:182-203, 2005.
Feldmann et al., "A Dwarf Mutant of *Arabidopsis* Generated by T-DNA Insertion Mutagenesis," *Science*, 243(4896):1351-1354, 1989.
Focks and Benning, "*wrinkled1*: A novel, low-seed-oil mutant of *Arabidopsis* with a deficiency in the seed-specific regulation of carbohydrate metabolism," *Plant Physiol.*, 118:91-101, 1998.
Girke et al., "Microarray analysis of developing *Arabidopsis* seeds," *Plant Physiol.*, 124:1570-1581, 2000.
Jako et al., "Seed-specific over-expression of an *Arabidopsis* cDNA encoding a diacylglycerol acyltransferase enhances seed oil content and seed weight," *Plant Physiol.*, 126(2):861-874, 2001.
James and Dooner, "Isolation of EMS-induced mutants in *Arabidopsis* altered in seed fatty acid composition," *Theor. Appl. Genet.*, 80(2):241-245, 1990.
Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409, 1995.
Katavic et al., "Utility of the *Arabidopsis FAE1* and yeast *SLC1-1* genes for improvements in erucic acid and oil content in rapeseed," *Biochem Soc. Trans.*, 28(6):935-937, 2000.
Larson et al., "Acyl CoA profiles of transgenic plants that accumulate medium-chain fatty acids indicate inefficient storage lipid synthesis in developing oilseeds," *Plant J.*, 32:519-527, 2002.
Lemieux et al., "Mutants of *Arabidopsis* with alterations in seed lipid fatty acid composition," *Theor. Appl. Genet.*, 80(2):234-240, 1990.

(Continued)

*Primary Examiner*—Elizabeth F McElwain
(74) *Attorney, Agent, or Firm*—Klarquist Sparkman LLP

(57) ABSTRACT

The present invention is directed to plants that display an altered oil content phenotype due to altered expression of a HIO30 nucleic acid. The invention is further directed to methods of generating plants with an altered oil content phenotype.

16 Claims, No Drawings

OTHER PUBLICATIONS

Lin et al., "The Pex16p homolog SSE1 and storage organelle formation in *Arabidopsis* seeds," *Science*. 284:328-330, 1999.

Lionneton et al., "Development of an AFLP-based linkage map and localization of QTLs for seed fatty acid content in condiment mustard (*Brassica juncea*)," *Genome*, 45(6):1203-1215, 2002.

Liu and Butow, "A transcriptional switch in the expression of yeast tricarboxylic acid cycle genes in response to a reduction or loss of respiratory function," *Mol. Cell. Biol.*, 19:6720-6728, 1999.

McCallum et al., "Targeted screening for induced mutations," *Nat. Biotechnol.*, 18(4):455-457, 2000.

Mekhedov et al., "Toward a functional catalog of the plant genome. A survey of genes for lipid biosynthesis," *Plant Physiol.*, 122:389-401, 2000.

Moire et al., "Impact of unusual fatty acid synthesis on futile cycling through β-oxidation and on gene expression in transgenic plants," *Plant Physiol.*, 134:432-442, 2004.

Neuhaus and Emes, "Nonphotosynthetic Metabolism In Plastids," *Annu. Rev. Plant Physiol. Plant Mol. Biol.*, 51:111-140, 2000.

O'Hara et al., "Fatty acid and lipid biosynthetic genes are expressed at constant molar ratios but different absolute levels during embryogenesis," *Plant Physiol.*, 129:310-320, 2002.

Okuley et al., "*Arabidopsis* FAD2 Gene Encodes the Enzyme That Is Essential for Polyunsaturated Lipid Synthesis," *Plant Cell*, 6:147-158, 1994.

Pritchard et al., "Germination and storage reserve mobilization are regulated independently in *Arabidopsis*," *Plant J.*, 31(5):639-647, 2002.

Rangasamy and Ratledge, "Compartmentation of ATP:Citrate lyase in plants," *Plant Physiol.*, 122:1225-1230, 2000.

Rangasamy and Ratledge, "Genetic enhancement of fatty acid synthesis by targeting rat liver ATP:citrate lyase into plastids of tobacco," *Plant Physiol.*, 122:1231-1238, 2000.

Ratledge et al, "Correlation of ATP/citrate lyase activity with lipid accumulation in developing seeds of *Brassica napus* L.," *Lipids*, 32(1):7-12, 1997.

Rawsthorne, S., "Carbon flux and fatty acid synthesis in plants," *Prog Lipid Res.*, 41:182-196, 2002.

Ruuska et al., "Contrapuntal networks of gene expression during *Arabidopsis* seed filling," *Plant Cell*, 14:1191-1206, 2002.

Rylott et al., "Co-ordinate regulation of genes involved in storage lipid mobilization in *Arabidopsis thaliana*," *Biochem Soc. Trans.*, 29:283-287, 2001.

Schnarrenberger and Martin, "Evolution of the enzymes of the citric acid cycle and the glyoxylate cycle of higher plants, A case study of endosymbiotic gene transfer," *Eur. J. Biochem.*, 269:868-883, 2002.

Schnurr et al., "Characterization of an acyl-CoA synthetase from *Arabidopsis thaliana*," *Biochem Soc.Trans.*, 28(6):957-958, 2000.

Shockey et al., "Characterization of the AMP-binding protein gene family in *Arabidopsis thaliana*: will the real acyl-CoA synthetases please stand up?" *Biochem Soc. Trans.*, 28(6):955-957, 2000.

Thelen et al., "Biotin carboxyl carrier protein isoforms in *Brassicaceae* oilseeds," *Biochem. Soc. Trans.*, 28(6):595-598, 2000.

Wada et al., "Role of a positive regulator of root hair development, CAPRICE, in *Arabidopsis* root epidermal cell differentiation," *Development*, 129(23):5409-5419, 2002.

White et al., "A new set of *Arabidopsis* expressed sequence tags from developing seeds. The metabolic pathway from carbohydrates to seed oil," *Plant Physiol.*, 124:1582-1594, 2000.

Yadav et al., "Cloning of higher plant omega-3 fatty acid desaturases," *Plant Physiol.*, 103(2):467-476, 1993.

Alcaraz et al., "Nucleotide sequence," Database accession No. Q9FT57, XP002367387, 2001.

\* cited by examiner

GENERATION OF PLANTS WITH ALTERED OIL CONTENT

REFERENCE TO RELATED APPLICATIONS

This is the §371 U.S. National Stage of International Application No. PCT/US2003/041146, filed on Dec. 18, 2003, which was published in English under PCT Article 21(2), and which in turn claims the benefit of U.S. provisional patent application No. 60/434,763 filed Dec. 18, 2002, both of which are hereby incorporated by reference.

BACKGROUND OF THE INVENTION

The ability to manipulate the composition of crop seeds, particularly the content and composition of seed oils, has important applications in the agricultural industries, relating both to processed food oils and to oils for animal feeding. Seeds of agricultural crops contain a variety of valuable constituents, including oil, protein and starch. Industrial processing can separate some or all of these constituents for individual sale in specific applications. For instance, nearly 60% of the US soybean crop is crushed by the soy processing industry. Soy processing yields purified oil, which is sold at high value, while the remainder is sold principally for lower value livestock feed (US Soybean Board, 2001 Soy Stats). Canola seed is crushed to produce oil and the co-product canola meal (Canola Council of Canada). Nearly 20% of the 1999/2000 US corn crop was industrially refined, primarily for production of starch, ethanol and oil (Corn Refiners Association). Thus, it is often desirable to maximize oil content of seeds. For instance, for processed oilseeds such as soy and canola, increasing the absolute oil content of the seed will increase the value of such grains. For processed corn it may be desired to either increase or decrease oil content, depending on utilization of other major constituents. Decreasing oil may improve the quality of isolated starch by reducing undesired flavors associated with oil oxidation. Alternatively, in ethanol production, where flavor is unimportant, increasing oil content may increase overall value. In many fed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors.

Biotechnological manipulation of oils can provide compositional alteration and improvement of oil yield. Compositional alterations include high oleic soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from ~3.5% to ~7%, improving the energy content of the grain.

While it has been fruitful, the HOC production system has inherent limitations. First, the system of having a low percentage of pollinators responsible for an entire field's seed set contains inherent risks, particularly in drought years. Second, oil contents in current HOC fields have plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

The most obvious target crops for the processed oil market are soy and rapeseed, and a large body of commercial work (e.g., U.S. Pat. No. 5,952,544; PCT application WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux B, et al. 1990, Theor Appl Genet 80, 234-240; James D W and Dooner H K (1990) Theor Appl Genet 80, 241-245). T-DNA mutagenesis screens (Feldmann et al., Science 243: 1351-1354, 1989) that detected altered fatty acid composition identified the omega 3 desaturase (FAD3) and delta-12 desaturase (FAD2) genes (U.S. Pat. No. 5,952,544; Yadav N S et al. (1993) Plant Physiol 103, 467-476; Okuley et al., Plant Cell. 1994 January; 6 (1):147-58). A screen which focused on oil content rather than oil quality, analyzed chemically-induced mutants for wrinkled seeds or altered seed density, from which altered seed oil content was inferred (Focks N and Benning C, Plant Physiol 118:91-101, 1998). Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al, Plant Physiol. 1995 May; 108 (1):399-409). It was further shown that seed-specific over-expression of the DGAT cDNA was associated with increased seed oil content (Jako et al., Plant Physiol. 2001 June; 126 (2):861-74).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., Science (1992) 258: 1350-1353; Weigel et al., Plant Physiology (2000) 122:1003-1013). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., Plant Cell (1996) 8:659-671, Schaffer et al., Cell (1998) 93: 1219-1229; Fridborg et al., Plant Cell (1999) 11: 1019-1032; Kardailsky et al., Science (1999) 286:1962-1965); Christensen S et al., 9$^{th}$ International Conference on *Arabidopsis* Research. Univ. of Wisconsin—Madison, Jun. 24-28, 1998. Abstract 165).

SUMMARY OF THE INVENTION

The invention provides a transgenic plant having a high oil phenotype. The transgenic plant comprises a transformation vector comprising a nucleotide sequence that encodes or is complementary to a sequence that encodes a HIO30 polypeptide. In preferred embodiments, the transgenic plant is selected from the group consisting of rapeseed, soy, corn, sunflower, cotton, cocoa, safflower, oil palm, coconut palm, flax, castor and peanut. The invention further provides a method of producing oil comprising growing the transgenic plant and recovering oil from said plant.

The transgenic plant of the invention is produced by a method that comprises introducing into progenitor cells of the plant a plant transformation vector comprising a nucleotide sequence that encodes or is complementary to a sequence that encodes a HIO30 polypeptide, and growing the transformed progenitor cells to produce a transgenic plant, wherein the HIO30 polynucleotide sequence is expressed causing the high oil phenotype.

DETAILED DESCRIPTION OF THE INVENTION

Definitions

Unless otherwise indicated, all technical and scientific terms used herein have the same meaning as they would to one skilled in the art of the present invention. Practitioners are particularly directed to Sambrook et al. Molecular Cloning: A Laboratory Manual (Second Edition), Cold Spring Harbor Press, Plainview, N.Y., 1989, and Ausubel F M et al. Current Protocols in Molecular Biology, John Wiley & Sons, New York, N.Y., 1993, for definitions and terms of the art. It is to be understood that this invention is not limited to the particular methodology, protocols, and reagents described, as these may vary.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected MRNA).

As used herein, a "plant cell" refers to any cell derived from a plant, including cells from undifferentiated tissue (e.g., callus) as well as plant seeds, pollen, progagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "altered oil content phenotype" refers to measurable phenotype of a genetically modified plant, where the plant displays a statistically significant increase or decrease in overall oil content (i.e., the percentage of seed mass that is oil), as compared to the similar, but non-modified plant. A high oil phenotype refers to an increase in overall oil content.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic.

Identification of Plants with an Altered Oil Content Phenotype

We used an *Arabidopsis* activation tagging screen to identify the association between the gene we have designated "HIO30," (At3g52260; GI#22331747:54-938), and an altered oil content phenotype (specifically, a high oil phenotype). Briefly, and as further described in the Examples, a large number of *Arabidopsis* plants were mutated with the pSKI015 vector, which comprises a T-DNA from the Ti plasmid of *Agrobacterium tumifaciens*, a viral enhancer element, and a selectable marker gene (Weigel et al, supra). When the T-DNA inserts into the genome of transformed plants, the enhancer element can cause up-regulation genes in the vicinity, generally within about 10 kilobase (kb) of the insertion. T1 plants were exposed to the selective agent in order to specifically recover transformed plants that expressed the selectable marker and therefore harbored T-DNA insertions. Samples of approximately 15-20 T2 seeds were collected from transformed T1 plants, and lipids were extracted from whole seeds. Gas chromatography (GC) analysis was performed to determine fatty acid content and composition of seed samples.

An *Arabidopsis* line that showed a high-oil phenotype was identified, wherein oils (i.e., fatty acids) constituted approximately 35% of seed mass. The association of the HIO30 gene with the high oil phenotype was discovered by analysis of the genomic DNA sequence flanking the T-DNA insertion in the identified line. Accordingly, HIO30 genes and/or polypeptides may be employed in the development of genetically modified plants having a modified oil content phenotype ("a HIO30 phenotype"). HIO30 genes may be used in the generation of oilseed crops that provide improved oil yield from oilseed processing and in the generation of feed grain crops that provide increased energy for animal feeding. HIO30 genes may further be used to increase the oil content of specialty oil crops, in order to augment yield of desired unusual fatty acids. Transgenic plants that have been genetically modified to express HIO30 can be used in the production of oil, wherein the transgenic plants are grown, and oil is obtained from plant parts (e.g. seed) using standard methods.

HIO30 Nucleic Acids And Polypeptides

*Arabidopsis* HIO30 nucleic acid (genomic DNA) sequence is provided in SEQ ID NO: 1 and in Genbank entry GI#22331747:54-938. The corresponding protein sequence is provided in SEQ ID NO:2 and in GI#22331748. Nucleic acids and/or proteins that are orthologs or paralogs of *Arabidopsis* HIO30, are described in Example 3 below.

As used herein, the term "HIO30 polypeptide" refers to a full-length HIO30 protein or a fragment, derivative (variant), or ortholog thereof that is "functionally active," meaning that the protein fragment, derivative, or ortholog exhibits one or more or the functional activities associated with the polypeptide of SEQ ID NO:2. In one preferred embodiment, a functionally active HIO30 polypeptide causes an altered oil content phenotype when mis-expressed in a plant. In a further preferred embodiment, mis-expression of the HIO30 polypeptide causes a high oil phenotype in a plant. In another embodiment, a functionally active HIO30 polypeptide is capable of rescuing defective (including deficient) endogenous HIO30 activity when expressed in a plant or in plant cells; the rescuing polypeptide may be from the same or from a different species as that with defective activity. In another embodiment, a functionally active fragment of a full length HIO30 polypeptide (i.e., a native polypeptide having the sequence of SEQ ID NO:2 or a naturally occurring ortholog thereof) retains one of more of the biological properties associated with the full-length HIO30 polypeptide, such as signaling activity, binding activity, catalytic activity, or cellular or extra-cellular localizing activity. A HIO30 fragment preferably comprises a HIO30 domain, such as a C- or N-terminal or catalytic domain, among others, and preferably comprises at least 10, preferably at least 20, more preferably at least 25, and most preferably at least 50 contiguous amino acids of a HIO30 protein. Functional domains can be identified using the PFAM program (Bateman A et al., 1999 Nucleic Acids Res 27:260-262; website at pfam.wustl.edu). A preferred HIO30 fragment comprises a pseudouridylate synthase domain (PFam00849). Functionally active variants of full-length HIO30 polypeptides or fragments thereof include polypeptides with amino acid insertions, deletions, or substitutions that retain one of more of the biological properties associated with the full-length HIO30 polypeptide. In some cases, variants are generated that change the post-translational processing of a HIO30 polypeptide. For instance, variants may have altered protein transport or protein localization characteristics or altered protein half-life compared to the native polypeptide.

As used herein, the term "HIO30 nucleic acid" encompasses nucleic acids with the sequence provided in or complementary to the sequence provided in SEQ ID NO:1, as well as functionally active fragments, derivatives, or orthologs thereof. A HIO30 nucleic acid of this invention may be DNA, derived from genomic DNA or cDNA, or RNA.

In one embodiment, a functionally active HIO30 nucleic acid encodes or is complementary to a nucleic acid that encodes a functionally active HIO30 polypeptide. Included within this definition is genomic DNA that serves as a template for a primary RNA transcript (i.e., an mRNA precursor) that requires processing, such as splicing, before encoding the functionally active HIO30 polypeptide. A HIO30 nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO30 polypeptide, or an intermediate form. A HIO30 polynucleotide can also include heterologous coding sequences, for example, sequences that encode a marker included to facilitate the purification of the fused polypeptide, or a transformation marker.

In another embodiment, a functionally active HIO30 nucleic acid is capable of being used in the generation of loss-of-function HIO30 phenotypes, for instance, via antisense suppression, co-suppression, etc.

In one preferred embodiment, a HIO30 nucleic acid used in the methods of this invention comprises a nucleic acid sequence that encodes or is complementary to a sequence that encodes a HIO30 polypeptide having at least 50%, 60%, 70%, 75%, 80%, 85%, 90%, 95% or more sequence identity to the polypeptide sequence presented in SEQ ID NO:2.

In another embodiment a HIO30 polypeptide of the invention comprises a polypeptide sequence with at least 50% or 60% identity to the HIO30 polypeptide sequence of SEQ ID NO:2, and may have at least 70%, 80%, 85%, 90% or 95% or more sequence identity to the HIO30 polypeptide sequence of SEQ ID NO:2. In another embodiment, a HIO30 polypeptide comprises a polypeptide sequence with at least 50%, 60%, 70%, 80%, 85%, 90% or 95% or more sequence identity to a functionally active fragment of the polypeptide presented in SEQ ID NO:2, such as a pseudouridylate synthase domain. In yet another embodiment, a HIO30 polypeptide comprises a polypeptide sequence with at least 50%, 60%, 70%, 80%, or 90% identity to the polypeptide sequence of SEQ ID NO:2 over its entire length and comprises a pseudouridylate synthase domain.

In another aspect, a HIO30 polynucleotide sequence is at least 50% to 60% identical over its entire length to the HIO30 nucleic acid sequence presented as SEQ ID NO: 1, or nucleic acid sequences that are complementary to such a HIO30 sequence, and may comprise at least 70%, 80%, 85%, 90% or 95% or more sequence identity to the HIO30 sequence presented as SEQ ID NO:1 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410; website at blast.wustl.edu/blast/README.html) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the nucleic acid sequence of SEQ ID NO: 1. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of SEQ ID NO:1 under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO30 polypeptide can be produced. For example, codons may be selected to increase the rate at which expression of the polypeptide occurs in a particular host species, in accordance with the optimum codon usage dictated by the particular host organism (see, e.g., Nakamura et al, 1999, Nucleic Acids Res 27:292). Such sequence variants may be used in the methods of this invention.

The methods of the invention may use orthologs of the *Arabidopsis* HIO30. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, supra; Dieffenbach C and Dveksler G (Eds.) PCR Primer: A Laboratory Manual, Cold Spring Harbor Laboratory Press, New York, 1989). For instance, methods for generating a cDNA library from the plant species of interest and probing the library with partially homologous gene probes are described in Sambrook et al, supra. A highly conserved portion of the *Arabidopsis* HIO30 coding sequence may be used as a probe. HIO30 ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known HIO30 polypeptides are used for ortholog isolation (see, e.g., Harlow E and Lane D, Using Antibodies: A Laboratory Manual, Cold Spring Harbor Laboratory Press, 1999, New York). Western blot analysis can determine that a HIO30 ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., supra. Once the candidate ortholog(s) are identified by any of these means, candidate orthologous sequence are used as bait (the "query") for the reverse BLAST against sequences from *Arabidopsis* or other species in which HIO30 nucleic acid and/or polypeptide sequences have been identified.

HIO30 nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., *Methods Enzymol.* 204:125-39, 1991), may be used to introduce desired changes into a cloned nucleic acid.

In general, the methods of the invention involve incorporating the desired form of the HIO30 nucleic acid into a plant expression vector for transformation of in plant cells, and the HIO30 polypeptide is expressed in the host plant.

An isolated HIO30 nucleic acid molecule is other than in the form or setting in which it is found in nature and is identified and separated from least one contaminant nucleic acid molecule with which it is ordinarily associated in the natural source of the HIO30 nucleic acid. However, an isolated HIO30 nucleic acid molecule includes HIO30 nucleic acid molecules contained in cells that ordinarily express HIO30 where, for example, the nucleic acid molecule is in a chromosomal location different from that of natural cells.

Generation of Genetically Modified Plants with an Altered Oil Content Phenotype

HIO30 nucleic acids and polypeptides may be used in the generation of genetically modified plants having a modified oil content phenotype. As used herein, a "modified oil content phenotype" may refer to modified oil content in any part of the plant; the modified oil content is often observed in seeds. In a preferred embodiment, altered expression of the HIO30 gene in a plant is used to generate plants with a high oil phenotype.

The methods described herein are generally applicable to all plants. Although activation tagging and gene identification is carried out in *Arabidopsis*, the HIO30 gene (or an ortholog, variant or fragment thereof) may be expressed in any type of plant. In a preferred embodiment, the invention is directed to oil-producing plants, which produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The invention may also be directed to fruit- and vegetable-bearing plants, grain-producing plants, nut-producing plants, rapid cycling *Brassica* species, alfalfa (*Medicago sativa*), tobacco (*Nicotiana*), turfgrass (Poaceae family), other forage crops, and wild species that may be a source of unique fatty acids.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an HIO30 polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.).

The optimal procedure for transformation of plants with Agrobacterium vectors will vary with the type of plant being transformed. Exemplary methods for Agrobacterium-mediated transformation include transformation of explants of hypocotyl, shoot tip, stem or leaf tissue, derived from sterile seedlings and/or plantlets. Such transformed plants may be reproduced sexually, or by cell or tissue culture. Agrobacterium transformation has been previously described for a large number of different types of plants and methods for such transformation may be found in the scientific literature. Of particular relevance are methods to transform commercially important crops, such as rapeseed (De Block et al., Plant Physiol. (1989) 91:694-701), sunflower (Everett et al., Bio/Technology (1987) 5:1201), and soybean (Christou et al., Proc. Natl. Acad. Sci USA (1989) 86:7500-7504; Kline et al., Nature (1987) 327:70).

Expression (including transcription and translation) of HIO30 may be regulated with respect to the level of expression, the tissue type(s) where expression takes place and/or developmental stage of expression. A number of heterologous regulatory sequences (e.g., promoters and enhancers) are available for controlling the expression of a HIO30 nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the 35S CaMV (Jones J D et al, Transgenic Res 1:285-297 1992), the CsVMV promoter (Verdaguer B et al., Plant Mol Biol 37:1055-1067, 1998) and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., Plant Mol Bio 21:625-640, 1993).

In one preferred embodiment, HIO30 expression is under control of regulatory sequences from genes whose expression is associated with early seed and/or embryo development. Legume genes whose promoters are associated with early seed and embryo development include *V. faba* legumin (Baumlein et al., 1991, Mol Gen Genet 225:121-8; Baumlein et al., 1992, Plant J 2:233-9), *V. faba* usp (Fiedler et al., 1993, Plant Mol Biol 22:669-79), pea *convicilin* (Bown et al., 1988, Biochem J 251:717-26), pea *lectin* (dePater et al., 1993, Plant Cell 5:877-86), *P. vulgaris* beta phaseolin (Bustos et al., 1991, EMBO J 10:1469-79), *P. vulgaris* DLEC2 and PHS [beta] (Bobb et al, 1997, Nucleic Acids Res 25:641-7), and soybean beta-*Conglycinin*, 7S storage protein (Chamberland et al., 1992, Plant Mol Biol 19:937-49). Cereal genes whose promoters are associated with early seed and embryo development include rice glutelin ("GluA-3," Yoshihara and Takaiwa, 1996, Plant Cell Physiol 37:107-11; "GluB-1," Takaiwa et al., 1996, Plant Mol Biol 30:1207-21; Washida et al., 1999, Plant Mol Biol 40:1-12; "Gt3," Leisy et al., 1990, Plant Mol Biol 14:41-50), rice *prolamin* (Zhou & Fan, 1993, Transgenic Res 2:141-6), wheat *prolamin* (Hammond-Kosack et al., 1993, EMBO J 12:545-54), maize *zein* (Z4, Matzke et al., 1990, Plant Mol Biol 14:323-32), and barley *B-hordeins* (Entwistle et al., 1991, Plant Mol Biol 17:1217-31). Other genes whose promoters are associated with early seed and embryo development include oil palm GLO7A (7S globulin, Morcillo et al., 2001, Physiol Plant 112:233-243), *Brassica napus* napin, 2S storage protein, and napA gene (Josefsson et al., 1987, J Biol Chem 262:12196-201; Stalberg et al., 1993, Plant Mol Biol 1993 23:671-83; Ellerstrom et al., 1996, Plant Mol Biol 32:1019-27), *Brassica napus* oleosin (Keddie et al., 1994, Plant Mol Biol 24:327-40), *Arabidopsis oleosin* (Plant et al., 1994, Plant Mol Biol 25:193-205), *Arabidopsis* FAEL (Rossak et al., 2001, Plant Mol Biol 46:717-25), *Canavalia gladiata* conA (Yamamoto et al., 1995, Plant Mol Biol 27:729-41), and *Catharanthus roseus* strictosidine synthase (Str, Ouwerkerk and Memelink, 1999, Mol Gen Genet 261:635-43). In another preferred embodiment, regulatory sequences from genes expressed during oil biosynthesis are used (see, e.g., U.S. Pat. No. 5,952,544). Alternative promoters are from plant storage protein genes (Bevan et al, 1993, Philos Trans R Soc Lond B Biol Sci 342:209-15).

In yet another aspect, in some cases it may be desirable to inhibit the expression of endogenous HIO30 in a host cell. Exemplary methods for practicing this aspect of the invention include, but are not limited to antisense suppression (Smith, et al., Nature 334:724-726, 1988; van der Krol et al., Biotechniques (1988) 6:958-976); co-suppression (Napoli, et al, Plant Cell 2:279-289, 1990); ribozymes (PCT Publication WO 97/10328); and combinations of sense and antisense (Waterhouse, et al., Proc. Natl. Acad. Sci. USA 95:13959-13964, 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., Proc. Natl. Acad. Sci. USA (1988) 85:8805-8809), a partial cDNA sequence including fragments of 5' coding sequence, (Cannon et al., Plant Molec. Biol. (1990) 15:3947), or 3' non-coding sequences (Ch'ng et al., Proc. Natl. Acad. Sci. USA (1989) 86:10006-10010). Cosuppression techniques may use the entire cDNA sequence (Napoli et al., supra; van der Krol et al., The Plant Cell (1990) 2:291-299) or a partial cDNA sequence (Smith et al., Mol. Gen. Genetics (1990) 224:477-481).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, Arch Virol Suppl 15:189-201, 1999]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., Cur Opin Plant Biol. 2(2):96-103, 1999; Dangond F, Physiol Genomics (2000) 2:53-58; van Hal N L et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Oil Content Phenotype

The invention further provides a method of identifying plants that have mutations in endogenous HIO30 that confer altered oil content, and generating altered oil content progeny of these plants that are not genetically modified. In one method, called "TILLING" (for targeting induced local lesions in genomes), mutations are induced in the seed of a plant of interest, for example, using EMS treatment. The resulting plants are grown and self-fertilized, and the progeny are used to prepare DNA samples. HIO30-specific PCR is used to identify whether a mutated plant has a HIO30 mutation. Plants having HIO30 mutations may then be tested for altered oil content, or alternatively, plants may be tested for altered oil content, and then HIO30-specific PCR is used to determine whether a plant having altered oil content has a mutated HIO30 gene. TILLING can identify mutations that may alter the expression of specific genes or the activity of proteins encoded by these genes (see Colbert et al (2001) Plant Physiol 126:480-484; McCallum et al (2000) Nature Biotechnology 18:455-457).

In another method, a candidate gene/Quantitative Trait Locus (QTLs) approach can be used in a marker-assisted breeding program to identify alleles of or mutations in the HIO30 gene or orthologs of HIO30 that may confer altered oil content (see Bert et al., Theor Appl Genet. 2003 June; 107 (1):181-9; and Lionneton et al, Genome. 2002 December; 45 (6):1203-15). Thus, in a further aspect of the invention, a HIO30 nucleic acid is used to identify whether a plant having altered oil content has a mutation in endogenous HIO30 or has a particular allele that causes altered oil content.

All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

Generation of Plants with a HIO30 Phenotype by Transformation with an Activation Tagging Construct Mutants were generated using the activation tagging "ACTTAG" vector, pSKI015 (GI#6537289; Weigel D et al., supra). Standard methods were used for the generation of *Arabidopsis* transgenic plants, and were essentially as described in published application PCT WO0183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4×CaMV 35S enhancer element. Transgenic plants were selected at the T1 generation based on herbicide resistance. T2 seed was collected from T1 plants and stored in an indexed collection, and a portion of the T2 seed was accessed for the screen.

Quantitative determination of seed fatty acid content was performed using the follows methods. An aliquot of 15 to 20 T2 seeds from each line tested, which generally contained homozygous insertion, homozygous wild-type, and heterozygous genotypes in a standard 1:1:2 ratio, was massed on UMT-2 ultra-microbalance (Mettler-Toledo Co., Ohio, USA) and then transferred to a glass extraction vial. Whole seeds were transesterified in 500 ul 2.5% $H_2SO_4$ in MeOH for 3 hours at 80° C., following the method of Browse et al. (Biochem J 235:25-31, 1986) with modifications. A known amount of heptadecanoic acid was included in the reaction as an internal standard. 750 ul of water and 400 ul of hexane were added to each vial, which was then shaken vigorously and allowed to phase separate. Reaction vials were loaded directly onto GC for analysis and the upper hexane phase was sampled by the autosampler. Gas chromatography with Flame Ionization detection was used to separate and quantify the fatty acid methyl esters. Agilent 6890 Plus GC's were used for separation with Agilent Innowax columns (30 m×0.25 mm ID, 250 um film thickness). The carrier gas was Hydrogen at a constant flow of 2.5 ml/minute. 1 ul of sample was injected in splitless mode (inlet temperature 220° C., Purge flow 15 ml/min at 1 minute). The oven was programmed for an initial temperature of 105° C., initial time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis was using the Millennium Chromatography Management System (Version 3.2, Waters Corporation, Milford, Mass.). Integration and quantification were performed automatically, but all analyses were subsequently examined manually to verify correct peak identification and acceptable signal to noise ratio before inclusion of the derived results in the study.

The ACTTAG line designated W000086431 was identified as having a high oil phenotype. Specifically, oil constituted 34.8% of seed mass (w/w) compared to an average oil content of 28.7% of other ACTTAG lines grown and analyzed in the same conditions (i.e. reference lines). Reanalysis of the same seed was performed in triplicate. Oil constituted 32.1% of seed mass, confirming an increase in oil content relative to reference.

The W000086431 line has three loci of T-DNA. One locus, was unlinked to the phenotype, and two closely linked loci were identified which cosegregated with the high oil phenotype. T2 individuals homozygous for the high oil loci produced seed with an oil content of 115.4% of the reference, T2 individuals hemizygous for the loci produced seed with an oil content of 118.4% of the reference. T2 individuals lacking the HIO-30 locus had oil contents of 105% of the reference. Because the homozygotes and hemizygotes for the high oil loci display a similar increase in oil content, it was determined that the high oil phenotype of W000068431 is dominant.

Example 2

Characterization of the T-DNA Insertion in Plants Exhibiting the Altered Oil Content Phenotype We performed standard molecular analyses, essentially as described in patent application PCT WO0183697, to determine the site of the T-DNA insertion associated with the altered oil content phenotype. Briefly, genomic DNA was extracted from plants exhibiting the altered oil content phenotype. PCR, using primers specific to the pSKI015 vector, confirmed the presence of the 35S enhancer in plants from line W000086431, and Southern blot analysis verified the genomic integration of the ACTTAG T-DNA.

Plasmid rescue and/or inverse PCR were used to recover genomic DNA flanking the T-DNA insertion, which was then subjected to sequence analysis using a basic BLASTN search and/or a search of the Arabidopsis Information Resource (TAIR) database (available at the arabidopsis.org website). Seeds from 18 T3 families descended from the mutant were harvested. The seed oil content of these families was determined as described in Example 1. The genotypes of these families with respect to a T-DNA insert were determined by T-DNA specific PCR using primers that are specific to one of the corresponding genomic region. The average oil content of T3 families containing the T-DNA insert at locus 2 and 3 was higher than those families lacking the insert at the corresponding loci. Therefore, we concluded that locus 2 and/or 3 is linked to the high oil phenotype. By contrast, the average oil content of T3 families containing the T-DNA insert at locus 1 was lower than/approximately the same as those families lacking the insert at the corresponding locus, and we concluded that locus 1 is not linked to the high oil phenotype.

Sequence analysis revealed that the start codon of the nucleotide sequence presented as SEQ ID NO: 1, which we designated HIO30, was approximately 5.6 kb 5' of the upstream border of the T-DNA insert at locus 3.

Example 3

Analysis of Arabidopsis HIO30 Sequence

Sequence analyses were performed with BLAST (Altschul et al., 1997, J. Mol. Biol. 215:403-410), PFAM (Bateman et al., 1999, Nucleic Acids Res 27:260-262), PSORT (Nakai K, and Horton P, 1999, Trends Biochem Sci 24:34-6), and/or CLUSTAL (Thompson J D et al, 1994, Nucleic Acids Res 22:4673-4680).

BLASTN of SEQ ID NO:1 against GenBank sequences identified 6 Arabidopsis ESTs derived from cDNA clones derived from the same genomic region as At3g52260. This gene appears to occur as a single copy in Arabidopsis.

BLASTN also identified additional ESTs from other plant species. The following three potato (Solanum tuberosum) ESTs were identified as candidate orthologs; BLAST scores are in parentheses: GI#s 13614224 (1054 4.2e41), 18257466 (1031 4.8e40), and 14266906 (1140 7.2e-50). Other plant ESTs were sorted by species, and then assembled into the least number of contigs, represented by SEQ ID NOs 3-6, and described further below. In most cases, the EST contigs represent partial coding regions. But, the entire cDNA sequence of the ortholog can be determined by someone skilled in molecular biology techniques.

SEQ ID NO:3 is from tomato (Lycoprsicon esculentum), and is a contig of the following sequences: GI#s 5894121, 9503437, 5894459, and 5889410. It has 56% identity with SEQ ID NO:1.

SEQ ID NO:4 is from soy (Glycine max), and is a contig of GI#s 6913831, and 5760781. It has 66% identity with SEQ ID NO:1.

SEQ ID NO:5 is from corn (Zea mays), and is a contig of GI#s 21215230, 5268759, and 22521540. It has 57% identity with SEQ ID NO:1.

SEQ ID NO:6 is from wheat (Triticum aestivum) and is a contig of GI#s 19955658 and 9364987. It has 62% identity with SEQ ID NO:1.

BLASTP analysis returned redundant entries for the At3g52260 gene product. The only other hits returned were numerous bacterial gene products corresponding to 23S RNA pseudouridylate synthase. No other plant sequences were returned.

PFam analysis detected an RNA pseudouridylate synthase domain (PF00849). In accordance with this functional prediction, PSORT2 predicts that the At3g52260 gene product is cytoplasmic (44%). The gene may have a regulatory function in the expression of genes involved in fatty acid metabolism or related pathways.

Example 4

Confirmation of Phenotype/Genotype Association

RT-PCR analysis showed that the HIO30 gene was over-expressed in plants from the line displaying the HIO30 phenotype. Specifically, RNA was extracted from rosette leaves and/or siliques of plants exhibiting the HIO30 phenotype collected at a variety of developmental stages and pooled. RT-PCR was performed using primers specific to the sequence presented as SEQ ID NO:1, to other predicted genes in the vicinity of the T-DNA insertion, and to a constitutively expressed actin gene (positive control). The results showed that plants displaying the HIO30 phenotype over-expressed the mRNA for the HIO30 gene, indicating the enhanced expression of the HIO30 gene is correlated with the HIO30 phenotype.

The dominant inheritance pattern of the HIO30 phenotype is confirmed through genetic analysis. In general, genetic analysis involves the production and analysis of F1 hybrids. Typically, F1 crosses are carried out by collecting pollen from T2 plants, which is used to pollinate wild type plants. Such crosses are carried out by taking approximately 4 flowers from each selected individual plants, and using the T2 flower as the male pollen donor and flowers of the wild type plants as the female. 4-5 crosses are done for an individual of interest. Seed formed from crosses of the same individual are pooled, planted and grown to maturity as F1 hybrids.

It is claimed:

1. A transgenic plant comprising a plant transformation vector comprising a nucleotide sequence that encodes a HIO30 polypeptide having at least 95% sequence identity with SEQ ID NO:2, wherein the HIO30 polypeptide can alter the oil phenotype of the transgenic plant, whereby the transgenic plant has a high oil phenotype relative to the non-transgenic control plant.

2. The transgenic plant of claim 1, which is selected from the group consisting of rapeseed, soy, corn, sunflower, cotton, cocoa, safflower, oil palm, coconut palm, flax, castor and peanut.

3. A plant part obtained from the plant according to claim 1.

4. The plant part of claim 3, which is a seed.

5. A method of producing oil comprising growing the transgenic plant of claim 1 and recovering oil from said plant.

6. A method of producing a high oil phenotype in a plant, said method comprising:
   a) introducing into progenitor cells of the plant a plant transformation vector comprising a nucleotide sequence that encodes a HIO30 polypeptide having at least 95% sequence identity with SEQ ID NO:2, wherein the HIO30 polypeptide can alter the oil phenotype of the transgenic plant, and
   b) growing the transformed progenitor cells to produce a transgenic plant, wherein said nucleotide sequence is expressed, and said transgenic plant exhibits an altered oil content phenotype relative to a non-transgenic control plant.

7. A plant obtained by the method of claim 6.

8. The plant of claim 7, which is selected from the group consisting of rapeseed, soy, corn, sunflower, cotton, cocoa, safflower, oil palm, coconut palm, flax, castor and peanut.

9. A transgenic plant comprising a plant transformation vector comprising a nucleotide sequence that encodes a HIO30 polypeptide having at least 95% sequence identity with SEQ ID NO:2.

10. The transgenic plant of claim 9, which is selected from the group consisting of rapeseed, soy, corn, sunflower, cotton, cocoa, safflower, oil palm, coconut palm, flax, castor and peanut.

11. A plant part obtained from the plant according to claim 9.

12. The plant part of claim 11, which is a seed.

13. A method of producing oil comprising growing the transgenic plant of claim 1 and recovering oil from said plant.

14. A method of producing a high oil phenotype in a plant, said method comprising:
   introducing into progenitor cells of the plant a plant transformation vector comprising a nucleotide sequence that encodes a HIO30 polypeptide having at least 95% sequence identity with SEQ ID NO:2, and
   growing the transformed progenitor cells to produce a transgenic plant, wherein said nucleotide sequence is expressed.

15. A plant obtained by the method of claim 14.

16. The plant of claim 14, which is selected from the group consisting of rapeseed, soy, corn, sunflower, cotton, cocoa, safflower, oil palm, coconut palm, flax, castor and peanut.

* * * * *

UNITED STATES PATENT AND TRADEMARK OFFICE
CERTIFICATE OF CORRECTION

PATENT NO.        : 7,566,816 B2
APPLICATION NO. : 10/539213
DATED             : July 28, 2009
INVENTOR(S)       : Lightner and Clendennen It is certified that error appears in the above-identified patent and that said Letters Patent is hereby corrected as shown below:

Column 14, line 15, "ul" should read --µl--.

Column 14, line 19, two occurrences of "ul" should read --µl-.

Column 14, line 27, "um" should read --µm--.

Column 14, line 28, "ul" should read --µl--.

Column 14, line 61, "W000068431" should read --W000086431--.

Column 15, line 54, "4.2e41" should read --4.2e-41--.

Column 15, line 55, "4.8e40" should read --4.8e-40--.

Column 34, Claim 13, "of claim 1" should read --of claim 9--.

Signed and Sealed this

Twenty-eighth Day of September, 2010

David J. Kappos
*Director of the United States Patent and Trademark Office*

SEQUENCE LISTING

```
<160> NUMBER OF SEQ ID NOS: 6

<210> SEQ ID NO 1
<211> LENGTH: 5034
<212> TYPE: DNA
<213> ORGANISM: Arabidopsis thaliana
```

<400> SEQUENCE: 1

```
atgccgcagg atcacgcttc gtgggatcgg aaagagctct tgaggcaaag gaaacacgat     60
aggcctgaac aatcttttga atccccgcct tttcgatgga gggattcgcc ttcttctcac    120
catgttcctc gagagttttc ttctcgtttg ggatctggag acttccgcag accttcttca    180
ttaacacagc tcttaagatt gataggaagt gaattgatga ggttactctt caaaggagca    240
attttaata ctcagggtgg acggcaccag tttgtggagg agactagtca tggatacaca     300
tcttctcggt ccagtgcccg aatgtttgat aattataggc catcagcatc gcgtggagac    360
tggagatata ccaggaattg cagggatgat agagtttctg taagccaaaa ggaatggaaa    420
tgcaatacat gggagatgag caacggatct tctagaagtt ttgagaggcc atttggtatt    480
agaaatggtc ggaggtcagt tgatgaaagg ccgctacatg cttcagatac tcattctacc    540
gtggtgaact ctttggatcc agccaactcg gctcattatc tggacaatga gatcagtacc    600
ccagtacggt ctcttaaaat taaaaatgag cataaatttt cagatcaaag gttatcactt    660
ccttcagatc ctcattctga atgtattagc ttgtttgaac ggccttcttc tgagaacaat    720
tatggcaata aggtttgttc accagcaaag caatgcaatg atttgatgta tggtcgaagg    780
ttagttagtg ataattcatt agatgctcca atccccaatg cagagctgga ggggacttgg    840
gaacaacttc gcctgaaaga cccgcaagat aacaatagtt tacatggtat caatgatata    900
gacggtgata ggaaatgtgc aaggagagt tctctgggag caactgggaa acttccactg     960
tggaatagtt ctgggagttt tgcatctcag agttcaggtt ttagtcattc aagtagcttg   1020
aaaagcttgg gggctgttga ttccagcgat cggaagattg aggttcttcc taaaattgtt   1080
actgtgactc aatcttcttc aggagacgct actgcctgtg ccacaactac tcatctttct   1140
gaggagatga gttctagaaa gaaacaacgt ctcgggtggg gtgagggact ggcgaaatat   1200
gagaaaaaga agttgatgt taacccaaat gaagatggaa caacattgat ggaaaacggt    1260
ttagaggaac tacattcgtt aaacaaaaat attgctgata aagtcccac agcagccatt     1320
gttccagatt atggttcccc tacaacacca tcctctgtag cttgcagttc atcaccaggg   1380
tttgctgata atcatctccc gaaggctgct atagctgcta gtgatgtcag taacatgtgc   1440
cgttcgccta gtcccgtgtc tagtattcac cttgaacgat tcccaatcaa tatcgaggag   1500
ctcgataaca tctcaatgga gcgttttggc tgtttactca atgagttact tggtactgat   1560
gattctggta caggggattc cagttctgtc caattgacat caatgaacac attacttgcc   1620
tggaaaggtg aaattttgaa agctgtggag atgactgaat cagaaattga tctccttgaa   1680
aacaaacata ggacactaaa gcttgaaggt agaagacact ctcgtgttgt tggacccagt   1740
tcatactgtt gtgatggaga tgcaaatgtg cccaaggagc aggcttcttg tagtttggat   1800
cctaaggcaa cagcttcttc tgtagctaaa acactggtga gagctcctgt gcatcaggct   1860
ggtttagcca aggttcctgc tgatgttttt gaagatagtc ctggggaagt taaacctcta   1920
tcccaatctt ttgccactgt tgaaagagag gaagatatac tgcccatacc atctatgaag   1980
gcagctgttt cttcgaaaga gattaacaca cctgcttttg ccaatcagga aactattgag   2040
gtttcttctg ctgatgacag catggcctcc aaagaagact tgttctgggc taagttatta   2100
tctgccaata gaaatatgc ttgtgaatca tctggagtat tcaatcaatt gcttccaaga   2160
gattttaatt cgtctgacaa ctcaagattc cctggcatat gtcaaacgca gtttgattct   2220
catgtccaag aaaaaattgc agatagggta ggcctattga gagctaggga gaaaatttta   2280
```

```
ctccttcagt ttaaagcgtt tcagctctca tggaagaaag atttggatca gctagcttta    2340
gcaaagtacc aatcaaagtc tagcaaaaaa acagaactat atccgaatgc aaaaaatgga    2400
gggtatctga agcttcccca atctgtacgc ctgaggttct cttcttcagc tccaagaagg    2460
gatagtgtag tccccacaac agagctcgta agttatatgg aaaagctact tccgggtacc    2520
catctaaagc cttttagaga cattttgaaa atgcctgcta tgattttgga tgagaaagag    2580
agggtgatgt cgaggtttat ttctagcaat ggactgatta agatccatg tgacgttgag     2640
aaggaaagaa caatgattaa tccttggacc tcagaggaga agaaatctt tctgaatttg     2700
ctagcaatgc atgggaagga tttcaagaag attgcttcat ctcttaccca aaagacaact    2760
gcggactgta ttgattacta ctacaaaaac cacaagtctg attgttttgg gaaaataaag    2820
aagcagcgtg cttatggtaa ggaagggaag cacacctaca tgttggctcc acgaaaaaag    2880
tggaaacgtg agatgggggc tgcctctctt gatattttag gggatgtctc cattatagca    2940
gcaaacgctg gaaaggttgc atcaaccagg ccgatctctt ccaaaaagat cacccttaga    3000
ggttgcagca gtgctaattc attgcagcac gatggaaata actctgaagg gtgctcctac    3060
agttttgatt tcccacgtaa gagaactgct ggtgcagatg ttttagctgt tggtcctttg    3120
tcaccagagc agataaattc ttgcttaagg acttctgtga gctctagaga gaggtgtatg    3180
gatcatctga gtttaatca tgtcgtaaag aaacctcgga tatctcatac tctacataat    3240
gagaacagca atactctaca caatgagaac agcaacgaag aagatgactc atgttcggaa    3300
gagagctgtg gggaaacagg tcctattcac tggacagatg atgagagatc tgcctttata    3360
cagggttttt cgcttttttgg caagaatttt gcttcaatat caaggtacgt cgggacaaga    3420
tctccagatc agtgtaaggt tttcttcagc aaagttcgga aatgtcttgg gttggaatct    3480
ataaagtttg gatctggaaa tgtaagcaca tccgtaagtg ttgataatgg caatgagggt    3540
ggtgggagcg acttggaaga tccttgtcct atggagagta actctggcat agtgaataat    3600
ggagtttgtg ccaagatggg tatgaattct cctacctcac cttttaatat gaatcaggat    3660
ggtgttaatc aatcaggctc tgcaaatgtg aaagccgacc ttagtagatc agaagaagag    3720
aatgggcaga atatttgtg tctgaaagat gataataatc tcgtgaacaa tgcatatgtc     3780
aatggcggtt tcccgagtct agtttcagaa tcttgtagag atttggtaga tattaatact    3840
gttgagagcc agtctcaggc tgccggaaaa agcaagagca atgatctcat gtcaatggaa    3900
atcgatgaag gtgtcttaac atctgtcact atatcttccg agccattgta ttgtggccta    3960
agtgttcttt ccaatgttat tgtggaaacc cctacagaaa tctcacgaaa gggctcagga    4020
gatcaaggtg ctacaatgcc taaatttagt tcaaagaatc aagatggagt gatgcaagct    4080
gcaaacagaa ccagaaattc tggccttgaa cctgaaagtg caccttcagg tttcaggtac    4140
cctgagtgtc ttcaccatgt tccgattgag gtgtgtacgg aaaaccctat aggcgtcagt    4200
gcaccacgag gaaatccaaa ttgccatgca gagtccgagt caggaaaattc tcttgttgga   4260
caagttgacg aaacacatga cttgggttgg cccaagaaca atctggaatt ggatgggagg    4320
cttcaggttt taggccatgt aaaccctgag cagattggtc tactaaaagc gaccaataca    4380
gaatcttgtc aaaatcccca gagatcagtc acccaagatc tgagcaggat aagtagatca    4440
aaatctgatt tgatcgtaaa aacccaacgt acaggtgaag gcttctcact caccaagtgt    4500
actagttcag ctcctaagcc tctggcagta tcccataaag agggcagatc tggtcatagc    4560
aggagccatt cgtttagttt gtctgatact gagagactcc acaagaatgg agatgtgaaa    4620
ctgtttggta cagtacttac tactgatgag aatggaataa aacaaaaaca caatccatgt    4680
```

```
ggaattgtca ggtcatcatc aaccttgagc agggaccatg atacaagaca tcattacatt      4740
aatcagcaac accttcagaa cgttcccatt acgagctacg gttttgggga tggcaacaga      4800
attcaaaccg ggctcacatc tttgccagag tcggccaagt tgcttgcaag ttgccctgaa      4860 gcatttcca cgcatctaaa gcagcaagtt ggtaacagca aagagattct ggtggatgtt       4920
aatggtggaa ttttgagctt tggtaagcat aacgaagata gagctgagtc ctcaagcgct      4980
aaggatgaag gtaacatagg aggggtaaat ggtgtagcag aggcagccac gtga            5034
```

<210> SEQ ID NO 2
<211> LENGTH: 1677
<212> TYPE: PRT
<213> ORGANISM: Arabidopsis thaliana

<400> SEQUENCE: 2

```
Met Pro Gln Asp His Ala Ser Trp Asp Arg Lys Glu Leu Leu Arg Gln
1               5                   10                  15

Arg Lys His Asp Arg Pro Glu Gln Ser Phe Glu Ser Pro Pro Phe Arg
            20                  25                  30

Trp Arg Asp Ser Pro Ser Ser His His Val Pro Arg Glu Phe Ser Ser
        35                  40                  45

Arg Leu Gly Ser Gly Asp Phe Arg Arg Pro Ser Ser Leu Thr Gln Leu
    50                  55                  60

Leu Arg Leu Ile Gly Ser Glu Leu Met Arg Leu Leu Phe Lys Gly Ala
65                  70                  75                  80

Ile Phe Asn Thr Gln Gly Gly Arg His Gln Phe Val Glu Glu Thr Ser
                85                  90                  95

His Gly Tyr Thr Ser Ser Arg Ser Ala Arg Met Phe Asp Asn Tyr
            100                 105                 110

Arg Pro Ser Ala Ser Arg Gly Asp Trp Arg Tyr Thr Arg Asn Cys Arg
        115                 120                 125

Asp Asp Arg Val Ser Val Ser Gln Lys Glu Trp Lys Cys Asn Thr Trp
    130                 135                 140

Glu Met Ser Asn Gly Ser Ser Arg Ser Phe Glu Arg Pro Phe Gly Ile
145                 150                 155                 160

Arg Asn Gly Arg Arg Ser Val Asp Glu Arg Pro Leu His Ala Ser Asp
                165                 170                 175

Thr His Ser Thr Val Val Asn Ser Leu Asp Pro Ala Asn Ser Ala His
            180                 185                 190

Tyr Leu Asp Asn Glu Ile Ser Thr Pro Val Arg Ser Leu Lys Ile Lys
        195                 200                 205

Asn Glu His Lys Phe Ser Asp Gln Arg Leu Ser Leu Pro Ser Asp Pro
    210                 215                 220

His Ser Glu Cys Ile Ser Leu Phe Glu Arg Pro Ser Ser Glu Asn Asn
225                 230                 235                 240

Tyr Gly Asn Lys Val Cys Ser Pro Ala Lys Gln Cys Asn Asp Leu Met
                245                 250                 255

Tyr Gly Arg Arg Leu Val Ser Asp Asn Ser Leu Asp Ala Pro Ile Pro
            260                 265                 270

Asn Ala Glu Leu Glu Gly Thr Trp Glu Gln Leu Arg Leu Lys Asp Pro
        275                 280                 285

Gln Asp Asn Asn Ser Leu His Gly Ile Asn Asp Ile Asp Gly Asp Arg
    290                 295                 300

Lys Cys Ala Lys Glu Ser Ser Leu Gly Ala Thr Gly Lys Leu Pro Leu
```

-continued

```
            305                 310                 315                 320
Trp Asn Ser Ser Gly Ser Phe Ala Ser Gln Ser Gly Phe Ser His
                325                 330                 335
Ser Ser Ser Leu Lys Ser Leu Gly Ala Val Asp Ser Ser Asp Arg Lys
                340                 345                 350
Ile Glu Val Leu Pro Lys Ile Val Thr Val Thr Gln Ser Ser Ser Gly
                355                 360                 365
Asp Ala Thr Ala Cys Ala Thr Thr His Leu Ser Glu Glu Met Ser
    370                 375                 380
Ser Arg Lys Lys Gln Arg Leu Gly Trp Gly Glu Gly Leu Ala Lys Tyr
385                 390                 395                 400
Glu Lys Lys Val Asp Val Asn Pro Asn Glu Asp Gly Thr Thr Leu
                405                 410                 415
Met Glu Asn Gly Leu Glu Glu Leu His Ser Leu Asn Lys Asn Ile Ala
                420                 425                 430
Asp Lys Ser Pro Thr Ala Ala Ile Val Pro Asp Tyr Gly Ser Pro Thr
                435                 440                 445
Thr Pro Ser Ser Val Ala Cys Ser Ser Ser Pro Gly Phe Ala Asp Lys
    450                 455                 460
Ser Ser Pro Lys Ala Ala Ile Ala Ala Ser Asp Val Ser Asn Met Cys
465                 470                 475                 480
Arg Ser Pro Ser Pro Val Ser Ser Ile His Leu Glu Arg Phe Pro Ile
                485                 490                 495
Asn Ile Glu Glu Leu Asp Asn Ile Ser Met Glu Arg Phe Gly Cys Leu
                500                 505                 510
Leu Asn Glu Leu Leu Gly Thr Asp Asp Ser Gly Thr Gly Asp Ser Ser
                515                 520                 525
Ser Val Gln Leu Thr Ser Met Asn Thr Leu Leu Ala Trp Lys Gly Glu
                530                 535                 540
Ile Leu Lys Ala Val Glu Met Thr Glu Ser Glu Ile Asp Leu Leu Glu
545                 550                 555                 560
Asn Lys His Arg Thr Leu Lys Leu Glu Gly Arg Arg His Ser Arg Val
                565                 570                 575
Val Gly Pro Ser Ser Tyr Cys Cys Asp Gly Asp Ala Asn Val Pro Lys
                580                 585                 590
Glu Gln Ala Ser Cys Ser Leu Asp Pro Lys Ala Thr Ala Ser Ser Val
                595                 600                 605
Ala Lys Thr Leu Val Arg Ala Pro Val His Gln Ala Gly Leu Ala Lys
                610                 615                 620
Val Pro Ala Asp Val Phe Glu Asp Ser Pro Gly Glu Val Lys Pro Leu
625                 630                 635                 640
Ser Gln Ser Phe Ala Thr Val Glu Arg Glu Glu Asp Ile Leu Pro Ile
                645                 650                 655
Pro Ser Met Lys Ala Ala Val Ser Ser Lys Glu Ile Asn Thr Pro Ala
                660                 665                 670
Phe Ala Asn Gln Glu Thr Ile Glu Val Ser Ser Ala Asp Asp Ser Met
                675                 680                 685
Ala Ser Lys Glu Asp Leu Phe Trp Ala Lys Leu Leu Ser Ala Asn Lys
                690                 695                 700
Lys Tyr Ala Cys Glu Ser Ser Gly Val Phe Asn Gln Leu Leu Pro Arg
705                 710                 715                 720
Asp Phe Asn Ser Ser Asp Asn Ser Arg Phe Pro Gly Ile Cys Gln Thr
                725                 730                 735
```

-continued

```
Gln Phe Asp Ser His Val Gln Glu Lys Ile Ala Asp Arg Val Gly Leu
            740                 745                 750

Leu Arg Ala Arg Glu Lys Ile Leu Leu Gln Phe Lys Ala Phe Gln
        755                 760                 765

Leu Ser Trp Lys Lys Asp Leu Asp Gln Leu Ala Leu Ala Lys Tyr Gln
        770                 775                 780

Ser Lys Ser Ser Lys Lys Thr Glu Leu Tyr Pro Asn Ala Lys Asn Gly
785                 790                 795                 800

Gly Tyr Leu Lys Leu Pro Gln Ser Val Arg Leu Arg Phe Ser Ser
                805                 810                 815

Ala Pro Arg Arg Asp Ser Val Val Pro Thr Thr Glu Leu Val Ser Tyr
                820                 825                 830

Met Glu Lys Leu Leu Pro Gly Thr His Leu Lys Pro Phe Arg Asp Ile
        835                 840                 845

Leu Lys Met Pro Ala Met Ile Leu Asp Glu Lys Glu Arg Val Met Ser
        850                 855                 860

Arg Phe Ile Ser Ser Asn Gly Leu Ile Glu Asp Pro Cys Asp Val Glu
865                 870                 875                 880

Lys Glu Arg Thr Met Ile Asn Pro Trp Thr Ser Glu Lys Glu Ile
                885                 890                 895

Phe Leu Asn Leu Leu Ala Met His Gly Lys Asp Phe Lys Lys Ile Ala
            900                 905                 910

Ser Ser Leu Thr Gln Lys Thr Thr Ala Asp Cys Ile Asp Tyr Tyr Tyr
            915                 920                 925

Lys Asn His Lys Ser Asp Cys Phe Gly Lys Ile Lys Lys Gln Arg Ala
        930                 935                 940

Tyr Gly Lys Glu Gly Lys His Thr Tyr Met Leu Ala Pro Arg Lys Lys
945                 950                 955                 960

Trp Lys Arg Glu Met Gly Ala Ala Ser Leu Asp Ile Leu Gly Asp Val
                965                 970                 975

Ser Ile Ile Ala Ala Asn Ala Gly Lys Val Ala Ser Thr Arg Pro Ile
            980                 985                 990

Ser Ser Lys Lys Ile Thr Leu Arg  Gly Cys Ser Ser Ala  Asn Ser Leu
        995                 1000                1005

Gln His  Asp Gly Asn Asn Ser  Glu Gly Cys Ser Tyr  Ser Phe Asp
        1010                1015                 1020

Phe Pro  Arg Lys Arg Thr Ala  Gly Ala Asp Val Leu  Ala Val Gly
        1025                1030                 1035

Pro Leu  Ser Pro Glu Gln Ile  Asn Ser Cys Leu Arg  Thr Ser Val
        1040                1045                 1050

Ser Ser  Arg Glu Arg Cys Met  Asp His Leu Lys Phe  Asn His Val
        1055                1060                 1065

Val Lys  Lys Pro Arg Ile Ser  His Thr Leu His Asn  Glu Asn Ser
        1070                1075                 1080

Asn Thr  Leu His Asn Glu Asn  Ser Asn Glu Glu Asp  Asp Ser Cys
        1085                1090                 1095

Ser Glu  Glu Ser Cys Gly Glu  Thr Gly Pro Ile His  Trp Thr Asp
        1100                1105                 1110

Asp Glu  Arg Ser Ala Phe Ile  Gln Gly Phe Ser Leu  Phe Gly Lys
        1115                1120                 1125

Asn Phe  Ala Ser Ile Ser Arg  Tyr Val Gly Thr Arg  Ser Pro Asp
        1130                1135                 1140
```

-continued

```
Gln Cys Lys Val Phe Phe Ser Lys Val Arg Lys Cys Leu Gly Leu
    1145                1150                1155

Glu Ser Ile Lys Phe Gly Ser Gly Asn Val Ser Thr Ser Val Ser
    1160                1165                1170

Val Asp Asn Gly Asn Glu Gly Gly Ser Asp Leu Glu Asp Pro
    1175                1180                1185

Cys Pro Met Glu Ser Asn Ser Gly Ile Val Asn Asn Gly Val Cys
    1190                1195                1200

Ala Lys Met Gly Met Asn Ser Pro Thr Ser Pro Phe Asn Met Asn
    1205                1210                1215

Gln Asp Gly Val Asn Gln Ser Gly Ser Ala Asn Val Lys Ala Asp
    1220                1225                1230

Leu Ser Arg Ser Glu Glu Asn Gly Gln Lys Tyr Leu Cys Leu
    1235                1240                1245

Lys Asp Asp Asn Asn Leu Val Asn Asn Ala Tyr Val Asn Gly Gly
    1250                1255                1260

Phe Pro Ser Leu Val Ser Glu Ser Cys Arg Asp Leu Val Asp Ile
    1265                1270                1275

Asn Thr Val Glu Ser Gln Ser Gln Ala Ala Gly Lys Ser Lys Ser
    1280                1285                1290

Asn Asp Leu Met Ser Met Glu Ile Asp Glu Gly Val Leu Thr Ser
    1295                1300                1305

Val Thr Ile Ser Ser Glu Pro Leu Tyr Cys Gly Leu Ser Val Leu
    1310                1315                1320

Ser Asn Val Ile Val Glu Thr Pro Thr Glu Ile Ser Arg Lys Gly
    1325                1330                1335

Ser Gly Asp Gln Gly Ala Thr Met Pro Lys Phe Ser Ser Lys Asn
    1340                1345                1350

Gln Asp Gly Val Met Gln Ala Ala Asn Arg Thr Arg Asn Ser Gly
    1355                1360                1365

Leu Glu Pro Glu Ser Ala Pro Ser Gly Phe Arg Tyr Pro Glu Cys
    1370                1375                1380

Leu His His Val Pro Ile Glu Val Cys Thr Glu Asn Pro Ile Gly
    1385                1390                1395

Val Ser Ala Pro Arg Gly Asn Pro Asn Cys His Ala Glu Ser Glu
    1400                1405                1410

Ser Gly Asn Ser Leu Val Gly Gln Val Asp Glu Thr His Asp Leu
    1415                1420                1425

Gly Trp Pro Lys Asn Asn Leu Glu Leu Asp Gly Arg Leu Gln Val
    1430                1435                1440

Leu Gly His Val Asn Pro Glu Gln Ile Gly Leu Leu Lys Ala Thr
    1445                1450                1455

Asn Thr Glu Ser Cys Gln Asn Pro Gln Arg Ser Val Thr Gln Asp
    1460                1465                1470

Leu Ser Arg Ile Ser Arg Ser Lys Ser Asp Leu Ile Val Lys Thr
    1475                1480                1485

Gln Arg Thr Gly Glu Gly Phe Ser Leu Thr Lys Cys Thr Ser Ser
    1490                1495                1500

Ala Pro Lys Pro Leu Ala Val Ser His Lys Glu Gly Arg Ser Gly
    1505                1510                1515

His Ser Arg Ser His Ser Phe Ser Leu Ser Asp Thr Glu Arg Leu
    1520                1525                1530

His Lys Asn Gly Asp Val Lys Leu Phe Gly Thr Val Leu Thr Thr
```

```
                1535                1540                1545

Asp Glu Asn Gly Ile Lys Gln Lys His Asn Pro Cys Gly Ile Val
    1550                1555                1560

Arg Ser Ser Ser Thr Leu Ser Arg Asp His Asp Thr Arg His His
    1565                1570                1575

Tyr Ile Asn Gln Gln His Leu Gln Asn Val Pro Ile Thr Ser Tyr
    1580                1585                1590

Gly Phe Trp Asp Gly Asn Arg Ile Gln Thr Gly Leu Thr Ser Leu
    1595                1600                1605

Pro Glu Ser Ala Lys Leu Leu Ala Ser Cys Pro Glu Ala Phe Ser
    1610                1615                1620

Thr His Leu Lys Gln Gln Val Gly Asn Ser Lys Glu Ile Leu Val
    1625                1630                1635

Asp Val Asn Gly Gly Ile Leu Ser Phe Gly Lys His Asn Glu Asp
    1640                1645                1650

Arg Ala Glu Ser Ser Ser Ala Lys Asp Glu Gly Asn Ile Gly Gly
    1655                1660                1665

Val Asn Gly Val Ala Glu Ala Ala Thr
    1670                1675

<210> SEQ ID NO 3
<211> LENGTH: 1012
<212> TYPE: DNA
<213> ORGANISM: Lycopersicon esculentum

<400> SEQUENCE: 3
caggaaattt gtagaatttg aatttgagtt taatatttg gccagaaatt tgttgatttc      60
ttcaagtttt ggattaatct gctgctgatt gtttcaggaa gttgcttctg gcgatattcc    120
ctactccgag ttacgaatgt cagaaaaagc agagcttgca gcggtgaggg cgtactttgg    180
agtgctgtgg ccgcaacgta atgagggatt atcctaccat gacatcgtcc gacccaccga    240
tgctggtctt acattgatcg aattctactt taggaagtac aaaaattcag ctcctttaca    300
aggttggttg cagagaattc aaaataaaca gataacaatt gatggtaaag ttgttatctt    360
accagatact gaactcagag caggtgctga attagtatat catcgccttc cttggagaga    420
acctgatgca ccttacttgc tagaagtact atttgaagat gactacttga ttgttgtaaa    480
taaaccttct ggtttgcaag ttcttcctgg agggttatat cagcagcgga ccgtcttgac    540
gcaactccag tggcatgcat gtaagctgac aaccacttcg tcaggttgtc aaaaaacaca    600
tccagtccca gttcatcgct taggaagggg tacatcagga atactgctct gtgcaaaaac    660
aaagctttgt aaatctcgcc ttgcagcata ttttgctgag gggacgtcag ttgttgaaga    720
aaaatgcacc aactcagagt gcaatacaat gaggaagatt tgcaagatat atcgggcgct    780
agtaagtggt gtgatggata tggatgaggc tgtcatcaag caaccaattg gtacaattaa    840
atatcctgga gttgctaaag ggttgtatgt tgcttctcct tcagggaagc cagctttgag    900
cagtgttcgc gttcttgaaa gagattcaga gagtaactgc acattggttc aggttgaaat    960
tcaatctgga aggccacacc aaatccgcat ccacctctct ttcataggat at           1012

<210> SEQ ID NO 4
<211> LENGTH: 737
<212> TYPE: DNA
<213> ORGANISM: Glycine max

<400> SEQUENCE: 4
```

| | |
|---|---:|
| cttggcctga atgcaacgac ggtctgtcct acgacgacgt cgttcgagcc tctgatgccg | 60 |
| gggcgacact catagagttt tactccacca agtacaagag ttctgctccc ttacaaggtt | 120 |
| ggttgcagcg aataaaaagt gggcagataa cagttgatgg aggagttgtt actgattcta | 180 |
| acacagtcct cagagttgga tcaaagctaa tctatcatag acttccatgg aaggagccag | 240 |
| atgcaccgca catgatcgac gtcttatatg aagatgatga catgattgct ctaaataaac | 300 |
| cgtctggcct gcaagttttg cctggaggtc tctaccagca gaggacaatt ttaacacagc | 360 |
| ttcaatggga agccaacaat cagggtacct gtgaaatgca caaaaggctg cattctggtc | 420 |
| ccgtgcatcg cctagggagg gggacttcag gaattttatt atgtgcgaag acaaaactag | 480 |
| ccagagctcg tcttgcatct cattttgctg acggaacttc tcacgttgga ggaaaaagag | 540 |
| atacaaagca ggaacttggg aagattgcaa agatgtaccg agctcttgtg agtgggatag | 600 |
| ttgagaatga caaggtgact attaatcaac caattggaat agtaaaatat cctggtgttg | 660 |
| ctaaagggtt atacgttgct tctgaatcag gaaaaccagc actcagtgta gtggacattc | 720 |
| tagagacgaa catacaa | 737 |

```
<210> SEQ ID NO 5
<211> LENGTH: 1308
<212> TYPE: DNA
<213> ORGANISM: Zea mays
<220> FEATURE:
<221> NAME/KEY: misc_feature
<222> LOCATION: (661)..(665)
<223> OTHER INFORMATION: n is a, c, g, or t
<220> FEATURE:
<221> NAME/KEY: misc_feature
<222> LOCATION: (1186)..(1186)
<223> OTHER INFORMATION: n is a, c, g, or t

<400> SEQUENCE: 5
```

| | |
|---|---:|
| gcacgaggcg gccgcggcag aaacacagat gggcgacggg gctccgccgc caggggctct | 60 |
| atactccttc ggaacgccgt ggccggagct caatcaaggc ctcacctaca ccgacacgtt | 120 |
| ccgttgcgct gatgcggacg ccgctaccac cttgattgag ttctactcta ctaaccacaa | 180 |
| gagctcggcg ccattgccag ggtggatcaa gaggattcgt aatgggcaga taaccgttga | 240 |
| tggtgaagtt gtcactgatc cagatatgac tctggtggat gggtctaagt tggtatatca | 300 |
| tcgttttcct tggcaggagc catttgcgcc gtatttgctg gaagtgctct acgaggatga | 360 |
| tgacatggtt gcccttaata agccttctgg cttgcaagtt ctgcctaaag gactgtttca | 420 |
| gcagcgaact gttttagcac agcttcaatt gaaagactgg aagatggcct catcttgccg | 480 |
| gttcaagaga aaagatgtgc agtcacatcc agtacctgtt catcgtttag ggaggggaac | 540 |
| atcaggcctc ctgctttgtg ccaagacaaa agttgccaaa gttcgacttg catcttattt | 600 |
| tgctgaaggt gctataaatg ctgcaaagaa aagggataaa tcagagttca gtgaagagcg | 660 |
| nnnnntttca aaattttatc gagccttagt gactggcata cttgatgatg atgaggttgt | 720 |
| tgttacgcaa cctatagggt tagttcatta tcctggagtt gcagagggac tttatgcagc | 780 |
| atgttcctca ggaaagccag caatgagcaa agtatgtgtt cttgagagac ttgcacacca | 840 |
| aaatcacaca ctggtccagg ttgaaattca ttcaggacga cctcaccaaa taaggataca | 900 |
| ccttgcatac attgggcacc cacttgtaga tgaccctctc tatggtattg gtgggcaccc | 960 |
| caattttgtt gagccagaat ctactggcac agatagttct tttgcatctg atgggggtta | 1020 |
| tgagagacct ttgcaacctg ttcctggaga ctgtgggtat cacctgcatg cacattggct | 1080 |
| ggttctttgc cacccaacaa ccaataagat ggtaaaaatt accgctcctc ttccacaaat | 1140 |

```
-continued tctacagaca cgggaggaac gccgcgctgc agctgagcaa accggnggtt gaacatgtag    1200
aatcttgaaa atgtatattt cttgaagtta gcaagcagca ggttctcaca gacgttagag    1260
ttagacactc agacatctgc tcctctgtca actgtacaac ggcgagct                 1308

<210> SEQ ID NO 6
<211> LENGTH: 566
<212> TYPE: DNA
<213> ORGANISM: Triticum aestivum

<400> SEQUENCE: 6
atactccgcc gctgcaggcg aactacgtct tcgggagggc atggccggat ctcaacgaag      60
gactctccta caccgatacg ttccgcggcg ctgatgcgga aaccaccgcc accttgacca     120
atttctactc tgagaactac aagagctcgg cgccattgcc agggtggatt cataggattc     180
gcaatggaca gataacggtt gatggccaag ttgtcactga tccagatatg attctcaggg     240
agggttctaa gttggtatat catcgcctcg catggaagga gccatttgca ccacatttgc     300
ttcaagtgct ttatgaagat gacgacatgg tagcccttaa taagccttcc ggtttgcaag     360
ttctgccaaa aggactcttc cagcagcgca ctgttctagc acaacttcag tggaaagagt     420
ggaagatgcc cccatcaagc tgctctaaga gaaaaaatgt gcagttacat cctgtacctg     480
ttcatcgatt aggaaggggc acgtcaggtc tactgctttg tgccaagaca aagcttgcca     540
aagttcaact tgcatcttat tttgca                                          566
```